United States Patent [19]

Schrader

[11] Patent Number: 5,135,735
[45] Date of Patent: Aug. 4, 1992

[54] METHOD OF LOCALIZING AND QUANTIFYING REGIONAL ENERGY METABOLISM IN A WARM-BLOODED LIVING BEING AND COMPOSITION THEREFOR

[75] Inventor: Jurgen Schrader, Düsseldorf, Fed. Rep. of Germany

[73] Assignee: Mallinckrodt Medical, Inc., St. Louis, Mo.

[21] Appl. No.: 573,007

[22] PCT Filed: Apr. 27, 1989

[86] PCT No.: PCT/NL89/00030
§ 371 Date: Dec. 14, 1990
§ 102(e) Date: Dec. 14, 1990

[30] Foreign Application Priority Data

Apr. 29, 1988 [DE] Fed. Rep. of Germany ....... 3814515

[51] Int. Cl.$^5$ .......................................... A61K 49/02
[52] U.S. Cl. ..................................... 424/1.1; 252/644
[58] Field of Search ........................... 424/1.1; 252/625

[56] References Cited

PUBLICATIONS

Duerre, J. A. et al. "Radioisotopically Labeled S-Ribosyl-L-Homocysteine," *J. Lab. Cmpos*, vol. 4(2), 1968, pp. 171–180.
Kredich, N. M. et al. "A Sensitive Radiochemical . . . and L-Homocysteine," *Anal Biochem*, V. 116(2), 1981, pp. 503–510.
Ueland, P. M. et al., "Homocysteine in Tissues of the Mouse & Rat," *J. Biol. Chem.*, V. 259(4), 1984, pp. 2360–2364.

*Primary Examiner*—John S. Maples
*Attorney, Agent, or Firm*—Evan R. Witt

[57] ABSTRACT

The invention relates to a method of localizing and quantifying regional energy metabolism, in particular regional ischemia, in a warm-blooded living being, comprising administering to said being a diagnostically effective quantity of a radiolabelled L-homocysteine or a radiolabelled functional derivative thereof. The invention further relates to a pharmaceutical composition to be used for performing the above method.

11 Claims, 1 Drawing Sheet

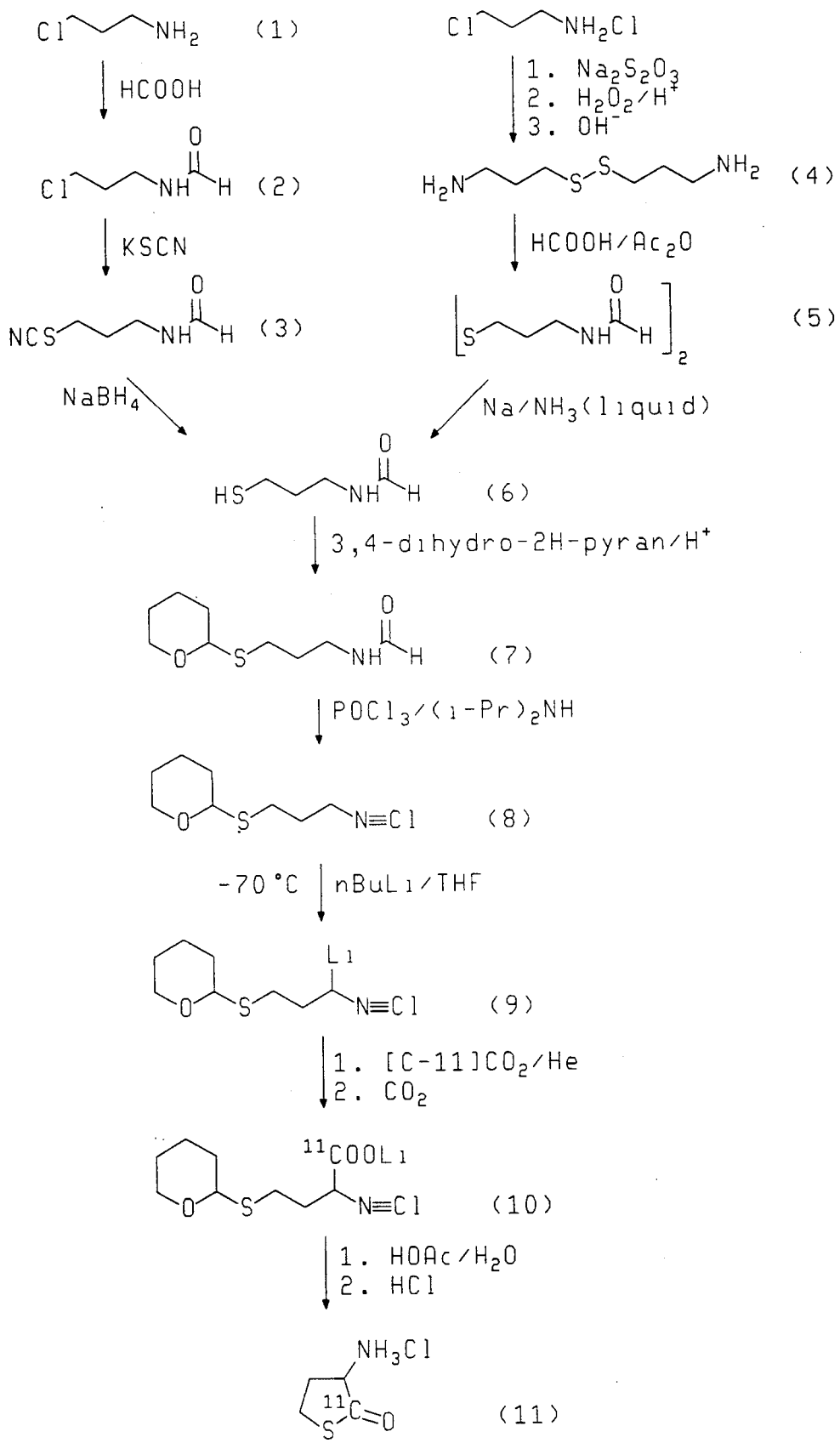

METHOD OF LOCALIZING AND QUANTIFYING REGIONAL ENERGY METABOLISM IN A WARM-BLOODED LIVING BEING AND COMPOSITION THEREFOR

The invention relates to a method of localizing and quantifying regional energy metabolism, in particular regional ischemia, in a warm-blooded living being. The invention further relates to a pharmaceutical composition to be used for said method.

The diagnosis and localisation of ischemia in various organs in present clinical practice relies mainly on angiographic methods and the study of tissue perfusion using thallium scintigraphy. While angiography permits the localisation of diseased arteries, it does not allow to draw conclusions as to the functional consequence and extent of the ischemic process. Furthermore, it is often difficult to relate changes in tissue perfusion to abnormalities observed with angiographic techniques. In order to gain information into the dynamics of tissue metabolism during ischemia use was made of various positron emitting tracer substances. Previous studies have largely relied upon only a few tracers for example N-13 ammonia for blood flow, C-11 palmitate for fatty acid metabolism and F-18 2--fluoro-2-desoxyglucose (FDG) for glucose utilisation. None of these tracers however, permitted a direct insight into the dynamics of the energy metabolism, mainly because the metabolism of substances applied differs greatly from organ to organ and is dependent on the dietary state of the organism.

Thallium scintigraphy is only a measure of tissue perfusion but not suitable for assessing the dynamics of energy metabolism. Therefore this method has a serious restriction in evaluating and quantifying ischemia. Radiolabelled fatty acids have the drawback, that their kinetic behaviour is seriously influenced by other substrates which play a role in the metabolism of the organs to be investigated.

BRIEF DESCRIPTION OF THE DRAWING

The FIGURE illustrates a possible chemical reaction scheme for preparing -homocysteine thiolactone, a precursor of -homocysteine.

It is the object of the invention to enable the localization and quantification of regional energy metabolism, in particular of regional ischemia, without invasive methods and avoiding the above disadvantages. It has been found that this object can be achieved according to the present invention by administering to a warm-blooded living being a diagnostically effective quantity of a radiolabelled L-homocysteine or a radiolabelled functional derivative thereof.

The quantity of radioactive material effective for diagnosing depends on various factors such as the diagnostic method, e.g. planar scintigraphy or emission tomography, the radiolabel used and the organ to be examined. In case the method of the invention is used to localize and quantify regional ischemia, such ischemia does not only encompass cardiac ischemia but also includes ischemia of other organs like the brains and the gastro-intestinal tract. It will be obvious from the above, that the quantity of radioactive material which is effective for diagnosing purposes may vary within broad ranges. Generally the radioactive material is administered to the living being in a quantity of 1 to 1000 MBq per 70 kg of body weight. The radiolabel may be chosen from radionuclides selected from the group consisting of positron emitting nuclides and gamma radiation emitting nuclides. Functional derivatives of L-homocysteine are to be understood to include derivatives of L-homocysteine wherein the S-H function is intact, or, in case the radiolabel is selenium-73, wherein the $^{73}$Se-H function is intact.

A preferred radiolabelled compound to be used for the method of the invention is L-homocysteine or its functional derivative, labelled with a radioisotope selected from the group consisting of carbon-11, selenium-73, fluoride 18, bromine-76, bromine-77 and iodine-123. Typical positron emitting nuclides like carbon-11, selenium-73 and fluorine-18 enable the in vivo application of the labelled compounds by using the so-called "positron-emission tomography" (PET) technique. By using this technique a computer tomogram can be obtained of the organ to be investigated, e.g. the heart or the brains, enabling the localization and quantification of regional energy metabolism. In the PET technique very short living radioisotopes are used which emit positrons, for example carbon-11 and fluorine-18 with half-lives of 20 and 110 minutes respectively. Gamma radiation emitting isotopes like bromine-76, bromine-77 and iodine-123 can be used for the labelling of compounds to be detected by conventional scanning techniques or in the so-called "single photon emission computer tomography" (SPECT) technique. By using conventional scanning techniques the emitted gamma radiation can be detected by suitable apparatuses, e.g. a gamma camera, to produce images of the organ to be investigated. The more advanced SPECT technique is also based upon the detection of gamma radiation by sensible detectors.

The invention further relates to a pharmaceutical composition to be used for the method defined before, comprising in addition to a pharmaceutically acceptable carrier and, if desired, at least one pharmaceutical acceptable adjuvant, as the active substance a radiolabelled L-homocysteine or a radiolabelled functional derivative thereof, in a diagnostically effective quantity. If desired, said composition may be brought into a form more suitable for intravenous or subcutaneous administration, for example by the addition of a pharmaceutically acceptable liquid vehicle, preferably a physiological saline solution. It will be evident, that the composition should be sterile for intravenous or subcutaneous administration. If desired, one or more adjuvants may be present in the composition, for example suitable stabilizers like ascorbic acid, gentisic acid or salts of these acids, and/or fillers like glucose, lactose mannitol etc. Dependent on the investigation to be performed and the results desired by performing these experiments, the composition may be administered to the living being, preferably a human being, at once, as a so-called bolus injection, or gradually by a continuous infusion.

The radiolabelled compounds can be prepared by methods which are known per se for related compounds by using readily available radiolabelled synthons like [C-11]$CO_2$, [C-11]$CH_3I$, [C-11]HCN, [C-11]CO, [F-18]$F_2$,[F-18]$CH_3CO_2F$ and [I-123]NaI. The use of [C-11]$CO_2$ for the preparation of 1-[C- 11]-homocysteine thiolactone: a precursor for carbon-11 labelled homocysteine, is described in the examples. The position of carbon-11 as the radiolabel in the homocysteine molecule is not relevant and can be chosen according to the ease of synthesizing the [C-11]homocysteine. Selenium-73 can be introduced as a radioactive label into the homocysteine molecule by substituting the mercapto group by a $^{73}$Se-H group. Radioactive halogen can be substituted for one of the hydrogen atoms at choice in the homocysteine molecule. The same holds, mutatis mutandis, for introducing a radioactive label in a functional derivative of homocysteine.

The invention will now be described in greater detail with reference to the ensuing specific examples.

EXAMPLE I

Preparation of (C11)-homocysteine thiolactone (11)

The preparation is carried out according to the reaction scheme illustrated in the FIGURE. The precursor, viz. S-(tetrahydropyranyl-(2))-3-thiopropyl isonitrile (8) is prepared starting with 3-chloropropylamine (1) via the intermediates 2 and 3. The oily formamide (2) is purified by distillation; intermediate (3) is purified by column chromatography. The alternative synthetic way (1→4→5) gives reasonably good yields with column chromatography of 5 only without purification of 4. The formamide of 3-mercaptopropylamine (6) is known e.g. from U.S. Pat. No. 3,278,526. This mercapto compound is converted into compound 7 with an equimolar quantity of 3,4-dihydro-2H-pyran in diethylether at room temperature; TSOH as a catalyst. Formamide 7 is dehydrated in the presence of excess diisopropylamine in dimethoxyethane as a solvent by slowly adding POCl$_3$ while cooling. The overall chemical yield of the precursor (8) synthesis is approx. 10%.

The labelling procedure is based on the carboxylation of the corresponding α-lithioisocyanide (9) with [C-11]CO$_2$ and subsequent hydrolysation and lactonisation. The labelling procedure is carried out in THF as a solvent. An equimolar quantity of n-butyllithium in hexane is added to a solution of the isonitrile precursor (8) in THF. The labelling is performed by flushing this solution while cooling with [C-11]CO2 in helium, followed by flushing with CO$_2$. Subsequent deprotection, hydrolysation and lactonisation of 10 with aqueous acetic acid and 6M hydrochloric acid successively yields the desired thiolactone (11). The thiolactone (11) obtained is purified by reverse phase HPLC with 0.1M sodium dihydrogenphosphate as an eluent. The radiochemical yield obtained is approx. 15%.

EXAMPLE II

Use of (C-11) homocysteine

Animal experiments were carried out in anaesthetized, thoracotomized dogs. (C-11)Homocysteine thiolactone (370 MBq) was given i.v. at a dose of 20 mg/kg either as bolus or over 3–10 min. The thiolactone administered is converted within the test animals to (C-11) homocysteine, the active species. Thereafter a side branch of the left anterior descending coronary artery was occluded. Imaging was performed with a positron emission tomograph (Scanditronix® PC-4096) and data were collected for 60 min. after the start of homocysteine infusion. Tracer concentration in plasma decreased with a T$_{\frac{1}{2}}$ of 40 min Topograms revealed that accumulation of tracer in the heart was strictly confirmed to the ischemic tissue.

I claim:

1. A method of localizing and quantifying regional energy metabolism in a warm-blooded living being, comprising:
   (a) administering to said being a diagnostically effective quantity of a radiolabelled L-homocysteine which has been radiolabelled with a radioisotope capable of emitting positron or gamma radiation; and
   (b) detecting positron or gamma radiation emissions from the radiolabelled L-homocysteine administered to said being, such that regional energy metabolism in the being is localized and quantified.

2. A method of localizing and quantifying regional energy metabolism as claimed in claim 1, wherein the radiolabelled L-homocysteine administered to the being is labelled with a radioisotope selected from the group consisting of carbon-11, selenium-73, fluorine-18, bromine-76, bromine-77 and iodine-123.

3. A method of localizing and quantifying regional energy metabolism as claimed in claim 1, wherein cardiac ischemia is localized and quantified.

4. A method of localizing and quantifying regional energy metabolism as claimed in claim 1, wherein brain ischemia is localized and quantified.

5. A method of localizing and quantifying regional energy metabolism as claimed in claim 1, wherein gastrointestinal ischemia is localized and quantified.

6. A method of localizing and quantifying regional energy metabolism as claimed in claims 1, 2, 3, 4, or 5, wherein the radiolabelled L-homocysteine is radiolabelled L-homocysteine thiolactone.

7. A method of localizing and quantifying regional energy metabolism as claimed in claim 6, wherein the radiolabelled L-homocysteine thiolactone administered to the being is labelled with a radioisotope selected from the group consisting of carbon-11, selenium-73, fluorine-18, bromine-76, bromine-77 and iodine-123.

8. A pharmaceutical composition for localizing and quantifying regional energy metabolism such as regional ischemia comprising:
   a pharmaceutically acceptable carrier and, optionally, at least one pharmaceutically acceptable adjuvant; and
   an active substance comprising a diagnostically effective quantity of a radiolabelled L-homocysteine which has been radiolabelled with a radioisotope capable of emitting positron or gamma radiation.

9. A pharmaceutical composition as claimed in claim 8, wherein the active substance is a L-homocysteine labelled with a radioisotope selected from the group consisting of carbon-11, selenium-73, fluorine-18, bromine-76, bromine-77 and iodine-123.

10. A pharmaceutical composition for localizing and quantifying regional energy metabolism as claimed in claim 8, wherein the active substance comprises a diagnostically effective quantity or radiolabelled L-homocysteine thiolactone.

11. A pharmaceutical composition as claimed in claim 10, wherein the L-homocysteine thiolactone is labelled with a radioisotope selected from the group consisting of carbon-11, selenium-73, fluorine-18, bromine-76, bromine-77 and iodine-123.

* * * * *